United States Patent [19]

Christensen et al.

[11] 4,208,422
[45] Jun. 17, 1980

[54] 1-SUBSTITUTED-PEN-2-EM-3-CARBOXYLIC ACIDS

[75] Inventors: Burton G. Christensen, Metuchen; David H. Shih, Edison, both of N.J.

[73] Assignee: Merck & Co., Inc., Rahway, N.J.

[21] Appl. No.: 954,273

[22] Filed: Oct. 24, 1978

[51] Int. Cl.² .................. C07D 487/04; A61K 31/40
[52] U.S. Cl. .............................. 424/274; 260/239 A; 260/326.31; 542/426
[58] Field of Search .................... 260/326.31; 424/274

[56] References Cited

U.S. PATENT DOCUMENTS

| 3,950,357 | 4/1976 | Kaher et al. ............ 260/326.31 |
| 4,153,714 | 5/1979 | Ponsford ................. 260/326.31 |

Primary Examiner—Mary C. Lee

Attorney, Agent, or Firm—James A. Arno; Julian S. Levitt

[57] ABSTRACT

Disclosed are 1-substituted-pen-2-em-3-carboxylic acids (I) and their pharmaceutically acceptable salts and esters which are useful as antibiotics; such compounds are prepared by total synthesis.

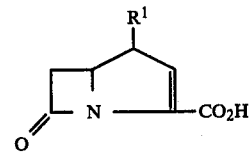

wherein $R^1$ is, inter alia, substituted and unsubstituted alkyl, aryl and aralkyl.

3 Claims, No Drawings

1-SUBSTITUTED-PEN-2-EM-3-CARBOXYLIC ACIDS

BACKGROUND OF THE INVENTION

This invention relates to 1-substituted-pen-2-em-3-carboxylic acids (I) and their pharmaceutically acceptable salts and esters which are useful as antibiotics. This invention also relates to a process for preparing such compounds, (I):

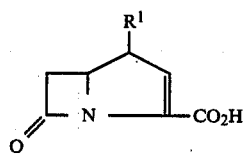

wherein $R^1$ is selected from the group consisting of substituted and unsubstituted: loweralkyl having from 1–6 carbon atoms; aralkyl such as phenylloweralkyl; aryl such as phenyl; cycloalkyl having from 3–6 carbon atoms; and cycloalkylalkyl having 1–3 carbon atoms in the alkyl moiety and 3–6 carbon atoms in the ring; wherein said ring or chain substituents on $R^1$ are selected from the group consisting of halo, such as chloro, bromo, fluoro and iodo, hydroxyl, amino, mono-, di-, and trialkylamino wherein the alkyl moiety has 1–6 carbon atoms; carboxyl, carbamoyl, amidino, guanidino, ureido, and the like.

There is a continuing need for new antibiotics. For unfortunately, there is no static effectiveness of any given antibiotic because continued wide scale usage selectively gives rise to resistant strains of pathogens. In addition, the new antibiotics suffer from the disadvantage of being effective only against certain types of microorganisms. Accordingly, the search for new antibiotics continues.

Thus, it is an objection of the present invention to provide a novel class of antibiotics (I) which are useful in animal and human therapy and in inanimate systems. These antibiotics are active against a broad range of pathogens which representatively include both gram positive bacteria such as *S. aureus*, *Strep. pyrogenes*, and *B. subtilis* and gram negative bacteria such as *E. coli*, *Proteus morganii*, Serratia, Pseudomonas and Klebsiella.

Further objects of this invention are to provide chemical processes for the preparation of such antibiotics and their non-toxic pharmaceutically acceptable salts and esters; pharmaceutical compositions comprising such antibiotics; and to provide methods of treatment comprising administering such antibiotics and compositions when an antibiotic effect is indicated.

DETAILED DESCRIPTION OF THE INVENTION

The compounds of the present invention (I, above) are conveniently prepared by the following scheme:

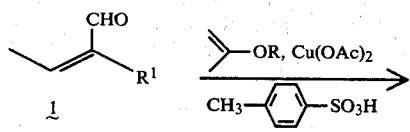

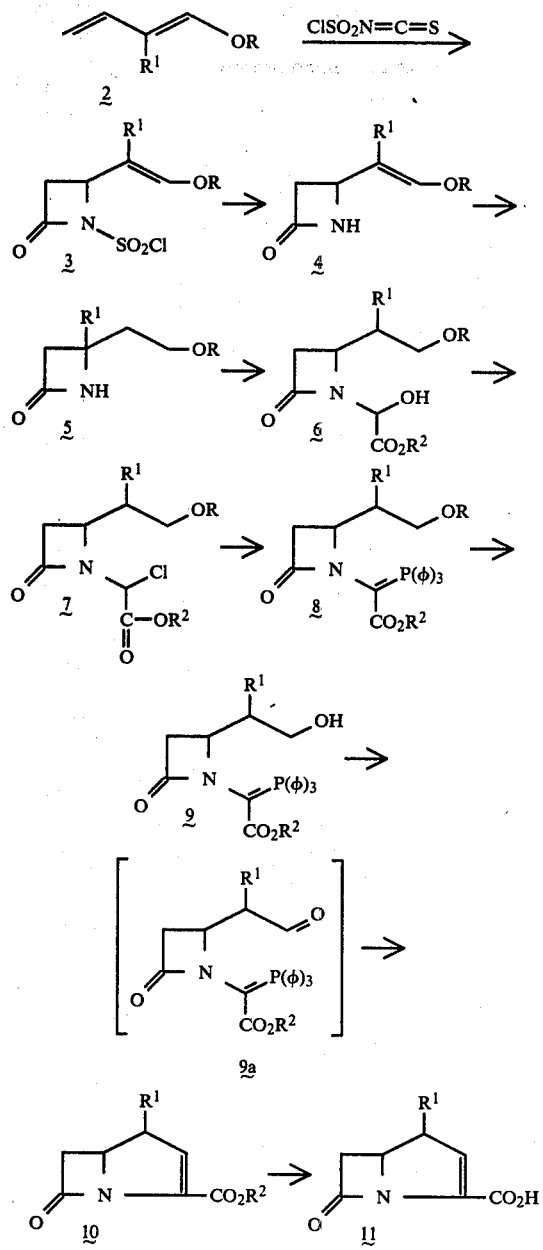

In words relative to the above diagram, the substituted azetidinone, 3 is prepared by reacting a $R^1$-substituted-R-oxybutadiene with chlorosulfonylisocyanate wherein R is an easily removable acyl blocking group such as an alkanoyl or aralkanoyl which bears no functional group or groups which might interefere with the desired course of reaction; and $R^1$ is as defined above relative to final product I. Species 2 is prepared by reacting an aldehyde 1 with a stoichiometric to 5 fold excess of an isopropenyl ester, for example, the acetate, with or without a solvent (suitable solvents include benzene, toluene, xylene, or the like) at a temperature of from 90° to 120° C. in the presence of 0.1 to 10 mole%, relative to 1 of cupric acetate, p-toluenesulfonic acid, or the like for from 4 to 10 hours to provide 2. As first explained, the reaction 2→3 is accomplished by treating 2 with a stoichiometric to 3 fold excess of chlorosulfonylisocyanate, the reaction is conducted without solvent or may be run in a solvent such as diethylether, ethylacetate, chloroform, methylene chloride, tetrahydrofuran, or the like at a temperature of −78° C. to 25° C. for from 0.5 to 2 hours. Intermediate species 3, converted to the sulfinamide by reduction, is then hydrolyzed to obtain 4 at pH 6-8. Typically the reaction solution comprising 3 is contacted (5-30 minutes) with an aqueous solution (10°-25° C.) of a reducing agent such as sodium sulfite, thiolylphenyl at pH 6-8 to provide 4. The reduction 4→5 is preferably by hydrogenation in a solvent such as ethylacetate, ethanol, methanol or the like in the presence of a metal catalyst such as platinum, palladium, rhodium or the like under a hydrogen pressure of from 1 to 40 atmospheres. Typically the reduction is complete in 2 to 6 hours. The reaction 5→6 is accomplished by treating 5 in a solvent such as benzene, toluene, xylene, or the like at a temperature of from 80° to 130° C. for from 1 to 8 hours with a glyxoylate ester, HCO-CO$_2$R$^2$, wherein R$^2$ is selected from the group consisting of o-nitrobenzyl, p-nitrobenzyl, o-dinitrobenzyl, benzyl or the like. The halogenation reaction 6→7 may be conducted by any of a variety of well known halogenation means. Suitable reagents include SOCl$_2$, POCl$_3$, oxalyl chloride and the like. A preferred means of chlorination involves treating 6 in a solvent such as tetrahydrofuran (THF), ether, CH$_2$Cl$_2$, and the like with thionyl chloride in the presence of 1-2 equivalents (relative to the thionyl chloride) of base such as pyridine, triethylamine, quinoline and the like. Typically the reaction is conducted at a temperature of from −30° to 25° C. for from 0.5 to 1 hour. The resulting intermediate species 7 is isolated if desired by conventional procedure for later reaction, 7→8. Intermediate 8 is prepared from 7 by treating 7 in a solvent such as dimethylformamide (DMF), dimethylsulfoxide (DMSO), THF, dimethoxyethane (DME) or the like with 1 to 1.5 equivalents of a phosphine such as triphenylphosphine, tributylphosphine, triethylphosphine, tris-(2-cyanoethyl)-phosphine or the like. Typically the reaction is conducted under a nitrogen atmosphere at a temperature of from 20° to 50° C., for from 0.5 to 2 hours. The reaction 8→9 may be achieved by any of a variety of well-known deblocking procedures such as hydrolysis or hydrogenolysis. A particularly convenient means for the deblocking 8→9, is by an alcoholysis procedure comprising treating 8 in a lower alkanol such as methanol, ethanol, or the like in the presence of 0.1 to 1.4 equivalents of the corresponding alkali metal alkoxide such as sodium methoxide or the like; typically the reaction is conducted at a temperature of from 0° to 25° C., for from 0.5 to 2 hours. The ring closure reaction 9→10 proceeds via the oxo intermediate 9a and is achieved by treating 9 with 1 to 10 equivalents of an oxidizing system such as 1:1 mixture of dimethylsulfoxide (DMSO) and acetic anhydride (Ac$_2$O); other oxidizing systems include trifluoroacetic anhydride in DMSO, cyclohexylcarbodiimide in DMSO, CrO$_3$.2(pyridine) in CH$_2$Cl$_2$, and pyridium chlorochromate in CH$_2$Cl$_2$, for example. Typically, the closure step 9→10 is conducted at a temperature of from about 0° to 100° C. for from 0.25 to 24 hours in the oxidative system (DMSO/Ac$_2$O) described above or by heating from 80°-160° C. (after isolation of the oxo compound 9a) in a solvent such as benzene, toluene, dioxane, xylene, or DMF. The carboxyl deblocking step 10→11 may be achieved by a number of well known procedures such as hydrolysis, hydrogenation, or photolysis of a suitable R$^2$ group. Suitably hydrogenation catalysts for deblocking include the platinum metals and their oxides such as palladium on carbon and the like; suitable solvents for the hydrogenation include methanol, dioxane/H$_2$O, ethanol/H$_2$O and the like in the presence of hydrogen at a pressure of from 1 to 50 atmospheres; the hydrogenation is typically conducted for from 5 min. to 4 hours at a temperature of about 25° C. in the optional presence of a mild base such as sodium bicarbonate or the like.

Typically, however, the carboxyl blocking is achieved by photolysis of the o-nitrobenzyl ester of 10 (R$^2$=o-nitrobenzyl) using 350 nm lamp in dioxane/H$_2$O in the presence of 1-2 equivalents of NaHCO$_3$ at 25° C. for 1-6 hours.

It will be recognized that the compounds of the present invention exists in two forms which may be designated α and β:

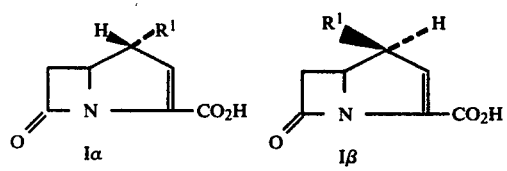

The α and β forms may be resolved at any stage after ring closure, but are preferably resolved at intermediate stage 9. Practically any chromatographic technique is suitable such as thin layer chromatograph, high pressure liquid chromatograph or silica gel column chromatograph or the like. The α and β isomers, separated at the level of 9, are present in an isomer ratio of from 1.2 to 2.0 in favor of β-isomer.

Typically, the separation is accomplished by silica gel chromatography, eluting with ethyl acetate; the α isomer of 9 is the less polar component of the two isomers.

With respect to starting reagent 2, its preparation is generally described in *J. Org. Chem.* 41, 2625 (1976) and *Helv. Chim. Acta* XLIV, 1, 1961.

An especially preferred preparation of 2 is by a modified procedure reported by W. J. Bailey, et al., [*J. Org. Chem.* 21, 328 (1956)] for the preparation of unsubstituted 1-acetoxyl-1,3-butadiene. A mixture of isopropenyl acetate and 2-methyl-2-butenal are heated at 90°-110° C. in the presence of a catalytic amount of p-toluenesulfonic acid and cupric acetate. The enol acetylation of 2-methyl-2-butenal is proceeded by constant removal of acetone from the mixture through a distillation head until the theoretical yield of acetone has been collected. The product is then isolated by distillation over N-phenyl-β-naphthamine under reduced pressure.

Especially preferred embodiments of the present invention are those wherein R$^1$ is selected from the group consisting of methyl, ethyl, propyl, isopropyl, cyclopropyl, phenyl, benzyl, and 2-bromoethyl.

The compounds made available by the present invention are valuable antibiotics active against various gram-positive and gram-negative bacteria and, accordingly, find utility in human and veterinary medicine. Such sensitive bacteria representatively include: *Staphylococcus aureus, Escherichia coli, Klebsiella pneumoniae,* Serratia, *Salmonella typhosa,* Pseudomonas and *Bacterium proteus.* The resulting compounds may further by utilized as additives to animal feed, for preserving foodstuffs, and as disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example, in waterbased paints and in the white water of paper mills to inhibit the growth of harmful bacteria.

These antibiotics may be used alone or in combination as an active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly.

Tablets and capsules for oral administration may be in unit dose presentation form, and may contain conventional excipients such as binding agents, for example, syrup, acacia, gelatin, sorbitol, tragacanth, or polyvinylpyrrolidone; fillers for example, lactose, sugar, maize-starch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, or syrups; or may be presented as a dry product, for reconstitution with water or other suitable vehicles before use. Such liquid preparations may contain conventional additives such as suspending agents, for example, sorbitol, syrup, methyl cellulose, glucose/-sugar syrup, gelatin, hydroxyethylcellulose, carboxymethyl cellulose, aluminum stearate gel or hydrogenated edible oils, for example almond oil, fractionated coconut oil, oily esters, propylene glycol, or ethyl alcohol; preservatives, for example methyl or propyl p-hydroxybenzoates or sorbic acid.

Compositions for injection may be presented in unit dose form in ampules, or in multidose container. The compositions may take forms as suspensions, solutions, or emulsions in oily or aqueous vehicles, and may contain formulatory agents such as suspending, stabilizing and/or dispersing agents. Alternatively, the active ingredient may be in powder form for reconstitution with a suitable vehicle, e.g., sterile, pyrogen-free water, before use.

The compositions may also be prepared in suitable forms for absorption through the mucous membranes of the nose and throat or bronchial tissues and may conveniently take the form of powder, liquid sprays, inhalants, lozenges, or throat paints. For medication of the eyes or ears, the preparations may be presented as individual capsules, in liquid or semi-solid form, or may be used as drops. Topical applications may be formulated in hydrophobic or hydrophilic bases as ointments, creams, or lotions.

Also, in addition to a carrier, the instant compositions may include other ingredients such as stabilizers, binders, antioxidants, preservatives, lubricators, suspending agents, viscosity agents or flavoring agents and the like. In addition, there may also be included in the compositions other active ingredients to provide a broader spectrum of antibiotic activity.

For veterinary medicine the composition may, for example, be formulated as an intramammary preparation in either long or quick-release bases.

The dosage to be administered depends to a large extent upon the general health and weight of the subject being treated, and the route and frequency of administration—the parenteral route being preferred for generalized infections and the oral route for intestinal infections. In general, a daily oral dosage consists of from about 2 to about 600 mg. of active ingredient per kg. of body weight of the subject in one or more applications per day. A preferred daily dosage for adult humans lies in the range of from about 15 to 150 mg. of active ingredient per kg. of body weight.

The instant compositions may be administered in several unit dosage forms as, for example, in solid or liquid orally ingestible dosage form. The compositions per unit dosage, whether liquid or solid may contain from 0.1 to 99% of active material, the preferred range being from about 10–60%. The composition will generally contain from about 15 mg. to about 1500 mg. of the active ingredient; however, in general, it is preferably to employ a dosage amount in the range of from about 100 mg. to 1000 mg. In parenteral administration the unit dosage is usually the pure compound in a slightly acidified sterile water solution or in the form of a soluble powder intended for solution.

Especially preferred pharmaceutically acceptable salts and esters involving the carboxyl group of compounds of the present invention (I) are disclosed and claimed in co-pending U.S. Patent Application Ser. No. 861,314 (filed 12-16-77) which application is directed, inter alia, to pharmaceutically acceptable salts and esters of the carboxyl group of thienamycin. It is precisely these salts and esters which are preferred in the present invention and they are prepared in a manner analogous to that disclosed in U.S. Patent Application Ser. No. 861,314, which is incorporated herein by reference. Thus, especially preferred salts include sodium, potassium, ammonium, and the like; and especially preferred esters include pivaloxymethyl, p-t-butylbenzyl, 5-indanyl, 3-phthalidyl, 3-methyl-2-butenyl, and the like. One should note than when, in the total synthesis outlined above, $R^2$ is a pharmaceutically acceptable ester moiety, there is no need for the final deblocking step if it is desired to have the final product I in the form of a pharmaceutically acceptable ester.

The following Examples illustrate, but do not limit, the product, process or compositional aspects of the invention. All temperatures are in °C.

EXAMPLE 1a

Preparation of Di-o-nitrobenzyltartarate

Tartaric acid (15.0 g, 0.1 mole) is dissolved in 40 ml. water and treated with lithium hydroxide (8.4 g, 0.2 mole). The resulting solution is evaporated to a small volume under reduced pressure and the residue is treated with p-dioxane. The resulting precipitate is filtered and dried under vacuum to give the di-lithium tartarate (17.7 g).

Di-lithium tartarate (9.46 g, 0.0585 mole) is suspended in 200 ml. DMF and treated with o-nitrobenzyl chloride (20 g, 0.117 mole) and sodium iodide (17.5 g, 0.117 mole). The mixture is stirred under $N_2$ for 2½ days at 65° C.

The solvent is removed under vacuum and the resulting paste is treated with water and sodium thiosulfate (5 g). The resulting solid is filtered and dried to give di-o-nitrobenzyltartarate (17.0 g, 0.040 mole, 69%, m.p. 128° C.).

n.m.r. (DMSO) :δ4.80(d, J=7.0 Hz, $\underline{H}$-C-OH), 5.23(d, J=7.0 Hz, H-C-$\underline{OH}$), 5.70(s, O-C$\underline{H}_2$-C$_6$H$_4$-NO$_2$); 7.73 & 8.20 (m, aromatic H).

Similar treatment of the di-lithium salt with R'X (where X=Cl, Br or I) such as p-nitrobenzylbromide, benzylbromide, pivalyoxymethyl chloride gives the corresponding di-ester of tartaric acid such as di-p-nitrobenzyl tartarate, di-benzyl tartarate, dipivaloyloxymethyl tartarate. These can be used as equivalent alternates to di-o-nitrobenzyl tartarate in Example 1, below.

EXAMPLE 1

Preparation of:

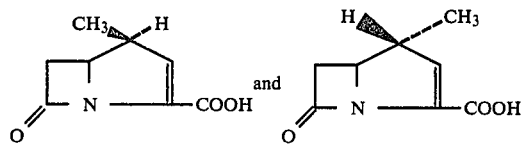

Step A

Preparation of 2

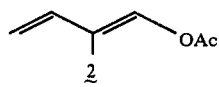

Isopropenyl acetate (182 g), cupric acetate (0.40 g), 2-methyl-2-butenal (84 g) and p-toluenesulfonic acid (1.52 g) are placed in a 1.0 l, three-necked flask equipped with a thermometer, a nitrogen inlet tube and a 10-in. Widmer column which is attached with a distillate head. The mixture is heated at 93°–110° C. until 73 ml of acetone is collected. After cooling to r.t. (25° C.) the mixture is filtered from solids. The dark brown filtrate is cooled in an ice-bath and mixed with 3.4 g triethanolamine in 200 ml water. The two layer mixture is distilled quickly at 53 mm (b.p. 54° C.). The organic layer of the distillate is separated. The aqueous layer is extracted with 200 ml ether. The organic layers are combined and washed with 10% K₂CO₃, dried over Na₂SO₄, and evaporated in vacuo. The residue so obtained is mixed with 2.0 g N-phenyl-β-napthamine and distilled under reduced pressure to give 2 (97 g), b.p. 81°–91° (66 mm). The structural confirmation is by nmr spectrum.

Step B

Preparation of 3 and 4

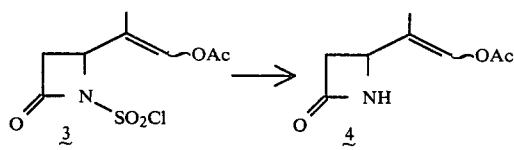

Chlorosulfonylisocyanate (CSI) (6.5 ml) is placed in a three-necked, 100-ml flask equipped with a thermometer, a magnetic stirring bar, a nitrogen inlet tube and a 25-ml pressure-equalized dropping funnel. The CSI is chilled to −50° C. and mixed with 12.5 ml ether through the dropping funnel. The etheral solution of CSI is allowed to warm up to −25° C.; to the solution is added dropwise 1-acetoxyl-2-methyl-1,3-butadiene (2) (5.9 ml in 12.5 ml ether) in 30 min. The mixture is then stirred for 20 min at −20°±3° C. The white precipitate formed initially is redissolved at the end of the reaction.

In a 500-ml round bottom flask, a solution of 10 g sodium sulfite and 25 g potassium hydrogen phosphate in 100 ml water is prepared and is cooled in an ice bath. Ether (100 ml) and crushed ice (100 g) are added and the mixture is vigorously stirred in an ice bath. At the end of 20 minutes reaction time, the reaction is transferred into the dropping funnel and added dropwise to the hydrolysis mixture in 5 minutes. The hydrolysis is allowed to continue for an additional 30 minutes at 3° C. The organic layer is separated and the aqueous is extracted with 50 ml ether. The organic layers are combined, dried over Na₂SO₄ and evaporated to give crystalline product 3 (2.3 g), m.p. 77°–78.5°; m.s. 169(M+); IR 1760 cm⁻¹ (β-lactam); NMR (300 MHz, CDCl₃): 1.70 (d), 2.16(s), 2.84 (qq), 3.18 (qq), 4.20 (m), 5.82 (broad, and 6.26 (s) ppm.

Step C

Preparation of 5

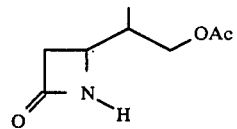

4-(1-methyl-2-acetoxyvinyl)azetidine-2-one (3) (6.5 g) is hydrogenated on a Parr shaker at r.t. under 40 psi hydrogen in the presence of 10% Pd/C (0.6 g) in 200 ml ethylacetate for 2 hr. The mixture is filtered from the catalyst and the filtrate is evaporated in vacuo to give the crude product. Purification of the crude product by high pressure liquid chromatograph (HPLC) (silical gel column, 30% ethylacetate/CH₂Cl₂ solvent system) affords a white crystalline product 5 (6.04 g) after evaporation of solvent. The product shows following physical characteristics: ms 171 (M+); IR(Neat) 1754 cm⁻¹; NMR (60 MHz, CDCl₃): 0.96 (d), 1.01 (d), 2.06 (d, OAc), 2.75–3.80 (m), 3.99 (d) and 6.80 (broad) ppm.

Step D

Preparation of 6

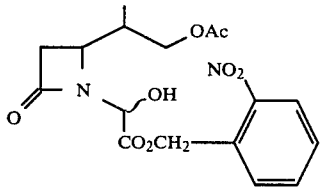

To the THF solution of o-nitrobenzyltartarate (424 mg, in 4 ml THF) is added periodic acid (272 mg in 4 ml THF) and stirred at r.t. for 30 min. The mixture is filtered and the filtrate is evaporated in vacuo to give crude o-nitrobenzylgloxylate. The crude product is taken up in benzene (20 ml) and filtered. The filtrate containing o-nitrobenzylgloxylate and 5 (169 mg) is placed in a 50-ml three-necked flask equipped with a Dean-Stark trap. The mixture is heated at reflux for 6 hr, then evaporated in vacuo to give crude product 6. Preparative TLC of the crude product (50% ethylacetate/CHCl₃ as solvent) gives 6 (308.6 mg) as white solids, m.s. 378 (M+); IR(CHCl₃) 1750 cm⁻¹ (β-lactam).

Step E

Preparation of 8

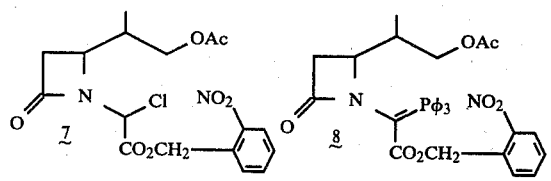

Under N₂ at −20° C., 6 (542 mg) in 5 ml THF is treated with thionyl chloride (204 mg) and pyridine (136 mg) for 10 min., then allowed to warm up to room temperature. The mixture is diluted with 10 ml benzene and filtered from solids. Evaporation of the mixture in vacuo gives 7 as oily residue. The residue is treated with triphenylphosphine (468 mg) in 5 ml DMF and stirred for 1 hr. at room temperature. The solvent is evaporated in vacuo then the residue is dissolved in 70 ml CHCl₃ and washed with 0.5 M sodium phosphate buffer (pH 7.2). The organic layer is separated, dried over Na₂SO₄ and evaporated to dryness to give crude product 8. Chromatographic purification (silica gel column 2.4×28 cm, 30% ethylacetate/CH₂Cl₂ as eluting solvent) of the crude product yields 0.61 g of 8, m.s. 624 (M+); IR (CHCl₃) 1748 (β-lactam) and 1634 cm⁻¹ (ylide ester) NMR (60 MHz, CDCl₃) 2.00 ppm (s, OAc).

Step F

Preparation of 9α and 9β

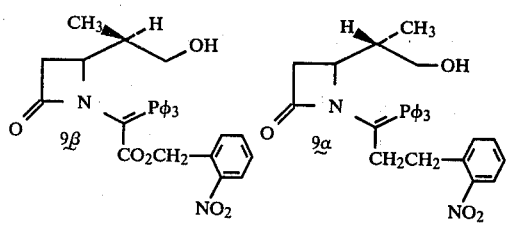

The ylide 8 (299 mg) is treated with sodium methoxide (2.5 mg) in MeOH (10 ml) at r.t. for 1 hr. then evaporated to dryness. The residue is chromatographed on TLC (silica gel GF) plates eluting with ethylacetate to separate and isolate 9α (178 mg) and 9β (29 mg). Both 9α and 9β show ms 582 (M+); IR (CHCl₃) 1736 and 1618 cm⁻¹.

Step G

Preparation of 10α

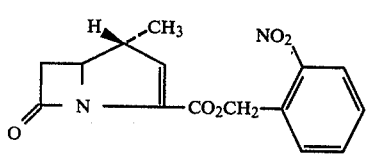

The ylide 9α (32 mg) is treated with 0.5 ml of DMSO and 0.5 ml acetic anhydride at r.t. overnight. The mixture is evaporated in vauco to give an oily residue which is chromatographed using preparative TLC (silica gel GF) eluting with 50% EtOAc/CH₂Cl₂ to give the desired product 10α (1.5 mg) and a by-product (10 mg). Product 10α shows ir (CHCl₃) 1777 cm⁻¹ (β-lactam); ms (E.I): 302 (M+); NMR (300 MHZ, CDCl₃) 1.15 (d), 2.17 (dd), 2.35 (dd), 2.27 (m), 4.38 (oct), 5.61 (d), 5.87 (d), 6.60 (d), 7.54 (t), 7.74 (t), 7.94 (d) and 8.18 ppm. The by-product is identified to be 12α, MS 642 (M+).

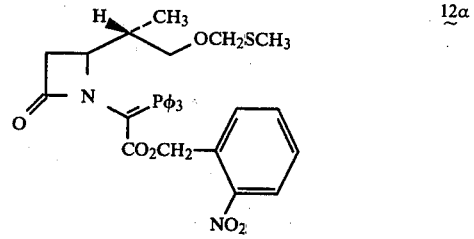

Step H

Preparation of 10β

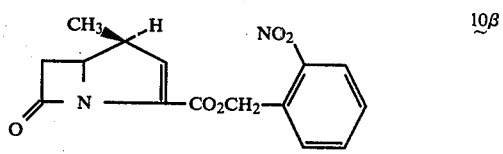

The ylide 9β (50 mg), 0.5 ml DMSO and 0.5 ml acetic anhydride are stirred at r.t. for 24 hr. The mixture is evaporated in vacuo to give crude products which are purified by preparative TLC (silica gel) eluting with 30% ethylacetate/cyclohexane to yield 10β (3 mg) and a by-product 12β (29 mg). The product 10β shows MS 302 (M+); IR (CHCl₃) 1776 cm⁻¹ (β-lactam); NMR (300 MHz, CDCl₃) 1.30 (d), 3.02 (q), 3.24 (t), 3.52 (q), 3.82 (m), 5.61 (d), 5.85 (d), 6.56 (d), 7.52 (t), 7.72 (t), 7.90 (d) and 8.17 (d). The by-product 12β shows MS 642 (M+).

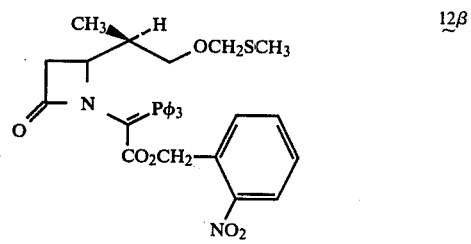

Step I

Preparation of 11β

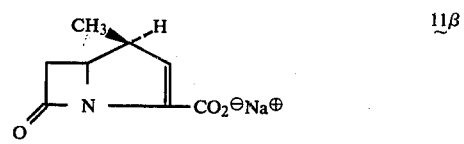

1β-methylcarbapenem-o-nitrobenzyl ester 10β (11 mg) is mixed with dioxane (1 ml), water (1 ml) and NaHCO₃ (3.1 mg). The mixture is photolysized (3500 Å) in a pyrex centrifuge tube at r.t. for 1 hr. The resulting solution is extracted with 3×2 ml ether, then 2×2 ml ethylacetate. The aqueous layer is separated and neutralized with dilute HCl to pH 7.0. The solution (0.7 ml) so obtained contains 0.13 mg (based on uv measurement) of the desired product 11β UVλ$_{max}^{H2O}$ 262 nm. A diluted solution assayed on MB-108 (S. aureus) agar plate shows 41 mm diameter zone (37° C., overnight). After lyophilization of the aqueous solution, white solid product 11β is obtained. NMR(300 MHz, D₂O) of 11β shows methyl doublet at 1.07 ppm.

Step J

Preparation of 11α

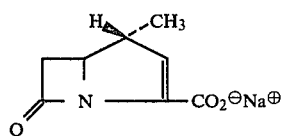

11α

1α-methylcarbapenem o-nitrobenzyl ester 10α (1.5 mg), 0.3 ml dioxane, 0.3 ml H₂O and 0.5 mg NaHCO₃ are placed in a pyrex centrafuge tube. The mixture is hydrogenated under 1 atm H₂ in the pressure of 2.0 mg 10% Pd/C for 10 min at r.t. The resulting solution is filtered from catalyst and the filtrate is extracted with ether (3×1 ml) and ethyl acetate (2×1 ml). The aqueous solution so obtained contains the desired product 11α, UVλ$_{max}^{H2O}$ 263 nm. A diluted solution of 11α placed on a ½" disc is assayed on a MB-108 agar plate and shows 48 mm diameter zone of inhibition.

EXAMPLE 2

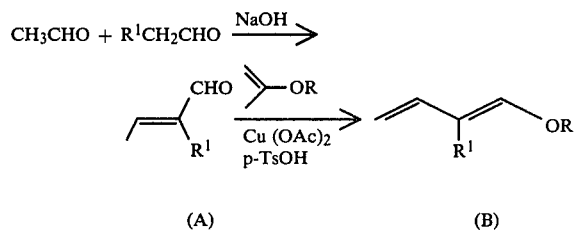

The α,β-unsaturated aldehydes (A) are prepared by a modified procedure reported by M. B. Green and W. J. Hickinbottom in *J. Chem. Soc.* 3262 (1957).

Acetaldehyde (1 eq.) and propionaldehyde (R¹=CH₃) (1 eq.) are placed in a three-necked round-bottom flask which is equipped with a mechanical stirrer, a dry-ice condenser, and a pressure equalized dropping-funnel. To the solution is added dropwise 1 eq. of 1 N NaOH through the dropping funnel with constant stirring. After completion of the mixing, the mixture is stirred for 10 min, then poured into a beaker containing crushed ice. Extraction of the mixture with ether gives the crude product. The desired product (A) is obtained by fractional distillation through a Widmer column.

Isopropenyl acetate (2 eq), cuprous acetate (0.002 eq), p-toluenesulfonic acid (0.008 eq.) and the α,β-unsaturated aldehyde (A) (1 eq) are placed in a three-necked round-bottom flask equipped with a thermometer, a nitrogen inlet tube and a Widmer column which is attached with a distillation head. The mixture is heated at 93°–110° C. until quantitative acetone is collected. The mixture is then allowed to cool to r.t. and filtered from solids. The dark brown filtrate is mixed with triethanolamine in water at 0° C. The two layer mixture is distilled quickly under reduced pressure. The organic layer of the distillate is separated. The aqueous layer is extracted with 200 ml ether. The combined organic layer is washed with 10% K₂CO₃, dried over Na₂SO₄, and evaporated in vacuo. The residue so obtained is mixed with 2.0 g N-phenyl-β-naphthamine and distilled under reduced pressure to give the desired 1-acetoxy-1,3-butadiene (B).

Following the procedure of Example 2, the following R¹ substituted species are obtained.

|  | R¹ | R |
|---|---|---|
| 1. | CH₃ | CH₃C(=O)— |
| 2. | CH₃CH₂ | CH₃C(=O)— |
| 3. | CH₃CH₂CH₂ | CH₃C(=O)— |
| 4. | (CH₃)₂CH | CH₃C(=O)— |
| 5. | cyclopropyl | CH₃C(=O)— |
| 6. | Ph— (Ph = phenyl) | CH₃C(=O)— |
| 7. | PhCH₂ | CH₃C(=O)— |

In the above table compound, 2–7 are obtained when the propanal of Example 2 is replaced by an equivalent amount of butanal, pentanal, 2-methyl-propanal, 2-cyclopropylethanal, 2-phenylethanal, 3-phenyl-propanal, and 4-bromo-butanal, respectively.

EXAMPLE 3

Following the procedure of Example 1 and utilizing the starting materials prepared in Example 2, the following representative species of the present invention are obtained.

|  | R¹ | R² |
|---|---|---|
| 1. | CH₃ | 2-NO₂-cyclohexyl-CH₂— |
| 2. | CH₃CH₂ | " |
| 3. | CH₃CH₂CH₂ | " |
| 4. | (CH₃)₂CH | " |
| 5. | cyclopropyl | " |
| 6. | Ph (Ph = phenyl) | O₂N—C₆H₄—CH₂ |
| 7. | PhCH₂ | " |

-continued

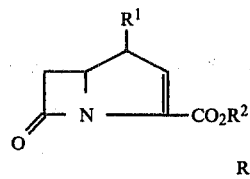

| | $R^1$ | $R^2$ |
|---|---|---|
| 8. | BrCH$_2$CH$_2$CH$_2$ | " |

EXAMPLE 4

Preparation of Pharmaceutical Compositions

One such unit dosage form is prepared by mixing 120 mg. of 1-methyl-pen-2-em-3-carboxylic acids with 20 mg of lactose and 5 mg of magnesium stearate. The 145 mg. mixture is placed into a No. 3 gelatin capsule. Similarly, by employing more of the active ingredient and less lactose, other dosage forms can be put up in No. 3 gelatin capsules and should it be necessary to mix more than 145 mg. of ingredients together, larger capsules such as compressed tablets and pills can also be prepared. The following examples are illustrative of the preparation of pharmaceutical formulations:

| TABLET | PER TABLET |
|---|---|
| 1-methyl-pen-2-em-3-carboxylic acids | 125 mg. |
| Dicalcium Phosphate | 192 mg. |
| Cornstarch, U.S.P. | 6 mg. |
| Lactose, U.S.P. | 190 mg. |
| Magnesium Stearate | Balance |

The active ingredient is blended with the dicalcium phosphate, lactose and about half of the cornstarch. The mixture is then granulated with 15% cornstarch paste (6 mg) and rough-screened. It is dried at 45° C. and screened again through No. 16 screens. The balance of the cornstarch and the magnesium stearate is added and the mixture is compressed into tablets, approximately 0.5 inch in diameter each weighing 800 mg.

| PARENTERAL SOLUTION | |
|---|---|
| Ampoule: | |
| 1-methyl-pen-2-em-3-carboxylic acids | 500 mg. |
| Diluent: Sterile Water for Injection | 2 cc |

| -continued | | |
|---|---|---|
| OPTHALMIC SOLUTION | | |
| 1-methyl-pen-2-em-3-carboxylic acids | | 100 mg. |
| Hydroxypropylmethyl Cellulose | | 5 mg. |
| Sterile Water | to | 1 ml. |
| OTIC SOLUTION | | |
| 1-methyl-pen-2-em-3-carboxylic acids | | 100 mg. |
| Benzalkonium chloride | | 0.1 mg. |
| Sterile water | to | 1 ml. |
| TOPICAL OINTMENT | | |
| 1-methyl-pen-2-em-3-carboxylic acids | | 100 mg. |
| Polyethylene Glycol 4000 U.S.P. | | 400 mg. |
| Polyethylene Glycol 400 U.S.P. | | 1.0 gram. |

The active ingredient in the above formulations may be administered alone or in combination with other biologically active ingredients as, for example, with other antibacterial agents such as lincomycin, a penicillin, streptomycin, novobiocin, gentamicin, neomycin, colistin and kanamycin, or with other therapeutic agents such as probenecid.

What is claimed is:

1. A compound having the formula:

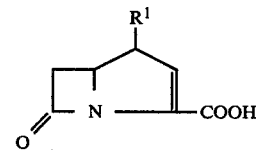

and its pharmaceutically acceptable salts; wherein $R^1$ is selected from the group consisting of substituted and unsubstituted loweralkyl having from 1–6 carbon atoms, phenyl, phenylloweralkyl, cycloalkyl having from 3 to 6 carbon atoms, and cycloalkylalkyl having 4 to 7 carbon atoms in the chain and 3–6 carbon atoms in the ring; wherein said substituents on $R^1$ are selected from the group consisting of halogen, hydroxyl, amino, mono-, di- and trialkylamino wherein the alkyl moiety has 1–6 carbon atoms, alkoxyl, azido, cyano, carboxyl, carbamoyl amidino, guanidino and ureido.

2. A compound according to claim 1 wherein $R^1$ is methyl, phenyl, ethyl, cyclopropyl, propyl and isopropyl.

3. An antibiotic pharmaceutical composition comprising a therapeutically effective amount of a compound according to claim 1 and a pharmaceutical carrier therefor.

* * * * *